(12) United States Patent
Schilling et al.

(10) Patent No.: US 12,138,441 B2
(45) Date of Patent: Nov. 12, 2024

(54) TETS COIL ALIGNMENT CONDITIONS ALGORITHM

(71) Applicant: Medtronic, Inc., Minneapolis, MN (US)

(72) Inventors: Eric A. Schilling, Ham Lake, MN (US); John Rudser, Miami, FL (US); David J. Peichel, Minneapolis, MN (US); Brian D. Kuhnley, Delano, MN (US)

(73) Assignee: Medtronic, Inc., Minneapolis, MN (US)

( * ) Notice: Subject to any disclaimer, the term of this patent is extended or adjusted under 35 U.S.C. 154(b) by 872 days.

(21) Appl. No.: 17/163,740

(22) Filed: Feb. 1, 2021

(65) Prior Publication Data

US 2021/0283392 A1 Sep. 16, 2021

Related U.S. Application Data

(60) Provisional application No. 62/988,434, filed on Mar. 12, 2020.

(51) Int. Cl.
*A61M 60/875* (2021.01)
*A61M 60/178* (2021.01)
(Continued)

(52) U.S. Cl.
CPC ........ *A61M 60/875* (2021.01); *A61M 60/178* (2021.01); *H02J 50/10* (2016.02); *H02J 50/90* (2016.02); *A61M 2205/04* (2013.01); *A61M 2205/3368* (2013.01); *A61M 2205/3576* (2013.01); *A61M 2205/50* (2013.01);
(Continued)

(58) Field of Classification Search
CPC .... A61M 60/875; A61M 60/178; H02J 50/90; H02J 50/10
See application file for complete search history.

(56) References Cited

U.S. PATENT DOCUMENTS

| | | |
|---|---|---|
| 7,997,854 B2 | 8/2011 | LaRose et al. |
| 8,419,609 B2 | 4/2013 | Shambaugh, Jr. et al. |

(Continued)

OTHER PUBLICATIONS

International Search Report and Written Opinion dated May 21, 2021, for corresponding International Application No. PCT/US2021/017162; International Filing Date: Feb. 9, 2021 consisting of 9-pages.

*Primary Examiner* — Mallika D Fairchild
*Assistant Examiner* — Thien Jason Tran
(74) *Attorney, Agent, or Firm* — Shumaker & Sieffert, P.A.

(57) ABSTRACT

A TETS having an external controller having a power source, a transmission coil in communication with the external controller, a receiving coil configured for transcutaneous inductive communication with the transmission coil, and an implantable controller in communication with the receiving coil and an implantable blood pump. The implantable controller has a battery configured to receive power from the receiving coil and the external controller is configured to categorize power transfer states based on predetermined thresholds of efficiency and power demand, and user display states (associated with optional configurable notifications) based on the power transfer states and predetermined temperature thresholds of the transmission coil.

16 Claims, 5 Drawing Sheets

(51) Int. Cl.
*H02J 50/10* (2016.01)
*H02J 50/90* (2016.01)

(52) U.S. Cl.
CPC . *A61M 2205/581* (2013.01); *A61M 2205/582* (2013.01); *A61M 2205/583* (2013.01); *A61M 2205/8206* (2013.01)

(56) References Cited

U.S. PATENT DOCUMENTS

| | | |
|---|---|---|
| 9,707,327 B2 | 7/2017 | Heilman et al. |
| 10,148,126 B2 | 12/2018 | Hoarau et al. |
| 10,149,933 B2 | 12/2018 | Bluvshtein et al. |
| 2006/0247737 A1* | 11/2006 | Olson ............... A61M 5/14276 607/33 |
| 2013/0289334 A1* | 10/2013 | Badstibner .............. H01F 38/14 307/104 |
| 2015/0290373 A1 | 10/2015 | Rudser et al. |
| 2015/0294550 A1 | 10/2015 | Kimball et al. |
| 2017/0063143 A1 | 3/2017 | Hoarau et al. |
| 2018/0280708 A1* | 10/2018 | Escalona ................. H02J 50/10 |
| 2019/0111198 A1 | 4/2019 | Bluvshtein et al. |
| 2019/0290819 A1 | 9/2019 | Hansen |

\* cited by examiner

Power transfer functional status    Temperature status

44 — Ideal

First Efficiency Threshold
greater than 80%
AND
iCTL power Threshold
less than 30W — 50
— 48

44 — Ideal

Temperature below 41°C
— 49

52 — Nominal

Second Efficiency Threshold
within the range of 65%-80%
AND
iCTL power Threshold
less than 30W — 60
— 56

Nominal - Slightly Elevated
52 —

Temperature within the range
of 41°C-43°C
— 58

62 — Marginal

Third Efficiency Threshold
within the range of 55%-65%
OR
Third Efficency Threshold
less than 90% and
iCTL power Threshold
greater than 30W
70 —
— 66
— 66

Marginal - Significantly Elevated
62 —

Temperature within the range
of 44°C-60°C
— 68

72 — Off

Fourth Efficiency Threshold
less than 70%
OR
iCTL power Threshold — 80
greater than 30W and/or
loss of power transfer
— 76

72 — Off - Extreme

Temperature above 60°C
— 78

Display Status

Alignment is Good

Power transfer status is ideal

46

Alignment is Ok
Power transfer status is
Nominal
AND/OR
Temperature is ideal

54

**Alignment is Marginal
and should be Improved**
Power transfer status is nominal and
temperature is slightly/significantly/
extremely elevated
OR
Power transfer status is marginal and
temperature is ideal/slightly elevated

64

**Alignment is Bad and
needs to be improved**
Power transfer is off
OR
Alignment is marginal and
temperatures are significantly/
extremely elevated

74

From Fig. 4

*FIG. 4 Continued*

TETS COIL ALIGNMENT CONDITIONS ALGORITHM

CROSS-REFERENCE TO RELATED APPLICATION

This application claims the benefit of U.S. Application Ser. No. 62/988,434, filed Mar. 12, 2020.

FIELD

The present technology is generally related to a system to provide status information, alerts, and notifications for an implantable transcutaneous energy transfer system (TETS).

BACKGROUND

Many implantable medical devices have significant energy requirements. A transcutaneous energy transfer system ("TETS") may be used to power implantable devices including artificial hearts, defibrillators, and electrical systems. Generally, a TETS can transfer energy from an external transmission coil to a receiving coil that is implanted under the skin. A TETS may be used to supplement, replace, or charge an implanted power source such as a rechargeable battery. Using a TETS to power these vital implantable devices can significantly lessen the potential of infection as the TETS does not require constant puncturing of the skin and/or wires that pass through the skin. Also, a patient may have increased mobility with the implantable device as power may be transmitted over a range of skin thicknesses.

Proper alignment of the external transmission coil and the implanted receiving coil is critical to transfer energy from the external transmission coil to the receiving coil through an area of the skin that separates the two coils. If sufficient alignment is not maintained between these two coils, interrupted operation of the implanted medical device may occur. Patient movement may cause the position of the external transmission coil and the receiving coil to shift and not be properly positioned to allow for the desired or required transfer of energy to power the implantable device and/or recharge an implantable battery.

SUMMARY

The techniques of this disclosure generally relate to a system for an implantable transcutaneous energy transfer system (TETS) that provides status information, alerts, and notifications.

In one aspect, the present disclosure provides for a transcutaneous energy transfer system (TETS), comprising: an external controller having a power source and a processing circuitry; a transmission coil in communication with the external controller; a receiving coil configured for transcutaneous inductive communication with the transmission coil; and an implantable controller in communication with the receiving coil and an implantable blood pump, the implantable controller having a battery configured to receive power from the receiving coil. The processing circuitry is configured to generate a first notification when either a power efficiency transfer between the transmission coil and the receiving coil drops below a first predetermined threshold or a temperature of the transmission coil rises above a first predetermined transmission coil temperature.

In another aspect of this embodiment, the disclosure provides that the processing circuitry is further configured to: generate a second notification when either the power efficiency transfer between the transmission coil and the receiving coil drops below a second predetermined threshold or a temperature of the transmission coil rises above a second predetermined transmission coil temperature; generate a third notification when either the power efficiency transfer between the transmission coil and the receiving coil drops below a third predetermined threshold or a temperature of the transmission coil rises above a third predetermined transmission coil temperature; and generate a fourth notification when either the power efficiency transfer between the transmission coil and the receiving coil is below a fourth predetermined threshold or there is a loss of power transfer between the transmission coil and the receiving coil.

In another aspect of this embodiment, the external controller further includes a display.

In another aspect of this embodiment, the display includes at least one of the group consisting of a first operating condition associated with the first notification, a second operating condition associated with the second notification, and a third operating condition associated with the third notification.

In another aspect of this embodiment, the first notification appears on the display when the first operating condition is generated, the second notification appears on the display when the second operating condition is generated, and the third notification appears on the display when the third operating condition is generated.

In another aspect of this embodiment, the second predetermined threshold is when the power efficiency transfer between the transmission coil and the receiving coil is within the range of 65-80%.

In another aspect of this embodiment, the third predetermined threshold is when the power efficiency transfer between the transmission coil and the receiving coil is within the range of 55-65%.

In another aspect of this embodiment, the second predetermined transmission coil temperature is 43° C. or greater than 43° C.

In another aspect of this embodiment, wherein the third predetermined transmission coil temperature is within the range of 44° C. and 60° C.

In another aspect of this embodiment, the first predetermined threshold is when the power efficiency transfer between the transmission coil and the receiving coil is above 80%.

In another aspect of this embodiment, wherein the first predetermined transmission coil temperature is when the temperature of the transmission coil is below 43° C.

In another embodiment, a TETS comprising: an external controller having a power source and a processing circuitry; a transmission coil in communication with the external controller; a receiving coil configured for transcutaneous inductive communication with the transmission coil; and an implantable controller in communication with the receiving coil and an implantable blood pump, the implantable controller having a battery configured to receive power from the receiving coil. The external controller having a display and a processing circuitry configured to: generate a first operating condition and a first notification on the display when either a power efficiency transfer between the transmission coil and the receiving coil drops below a first predetermined threshold and has an internal power demand less than a first predetermined threshold or a temperature of the transmission coil rises above a first predetermined transmission coil temperature; generate a second operating condition and a second notification on the display when either the power efficiency transfer between the transmission coil and the receiving coil drops below a second predetermined threshold and has an internal power demand less than the first predetermined threshold or a temperature of the transmission coil rises above a second predetermined transmission coil temperature; and generate a third operating condition and a third notification on the display when either the power efficiency transfer between the transmission coil and the receiving coil drops below a third predetermined threshold and has an internal power demand less than the first predetermined threshold or a temperature of the transmission coil rises above a third predetermined transmission coil temperature.

In another aspect of this embodiment, the first predetermined threshold is when the power efficiency transfer between the transmission coil and the receiving coil is greater than 80%.

In another aspect of this embodiment, the second predetermined threshold is when the power efficiency transfer between the transmission coil and the receiving coil is within the range of 65-80%.

In another aspect of this embodiment, the third predetermined threshold is when the power efficiency transfer between the transmission coil and the receiving coil is within the range of 55-65%.

In another aspect of this embodiment, the first predetermined transmission coil temperature is when the temperature of the transmission coil is below 43° C.

In another aspect of this embodiment, the second predetermined transmission coil temperature is when the temperature of the transmission coil is within the range of 43° C. and 55° C.

In another aspect of this embodiment, the third predetermined transmission coil temperature is when the temperature of the transmission coil is within the range of 50° C. and 60° C.

In another aspect of this embodiment, the first notification, the second notification, and the third notification are at least one of the group consisting of an audible notification, a visual notification, or a tactile notification.

In another embodiment, a TETS comprises: an external controller having a power source and a processing circuitry; a transmission coil in communication with the external controller; a receiving coil configured for transcutaneous inductive communication with the transmission coil; and an implantable controller in communication with the receiving coil and an implantable blood pump, the implantable controller having a battery configured to receive power from the receiving coil. The external controller having a display and a processing circuitry configured to: generate a first operating condition and a first notification on the display when either a power efficiency transfer between the transmission coil and the receiving coil is above 80% and an internal controller power demand is less than 30 Watts or a temperature of the transmission coil is below 43° C.; generate a second operating condition and a second notification on the display when either the power efficiency transfer between the transmission coil and the receiving coil is within the range of 65-80% and an internal controller power demand is less than 30 Watts or a temperature of the transmission coil is greater than 43° C.; and generate a third operating condition and a third notification on the display when either the power efficiency transfer between the transmission coil and the receiving coil is within the range of 55-65% or a temperature of the transmission coil is within the range of 50° C. and 60° C.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Figure 1:
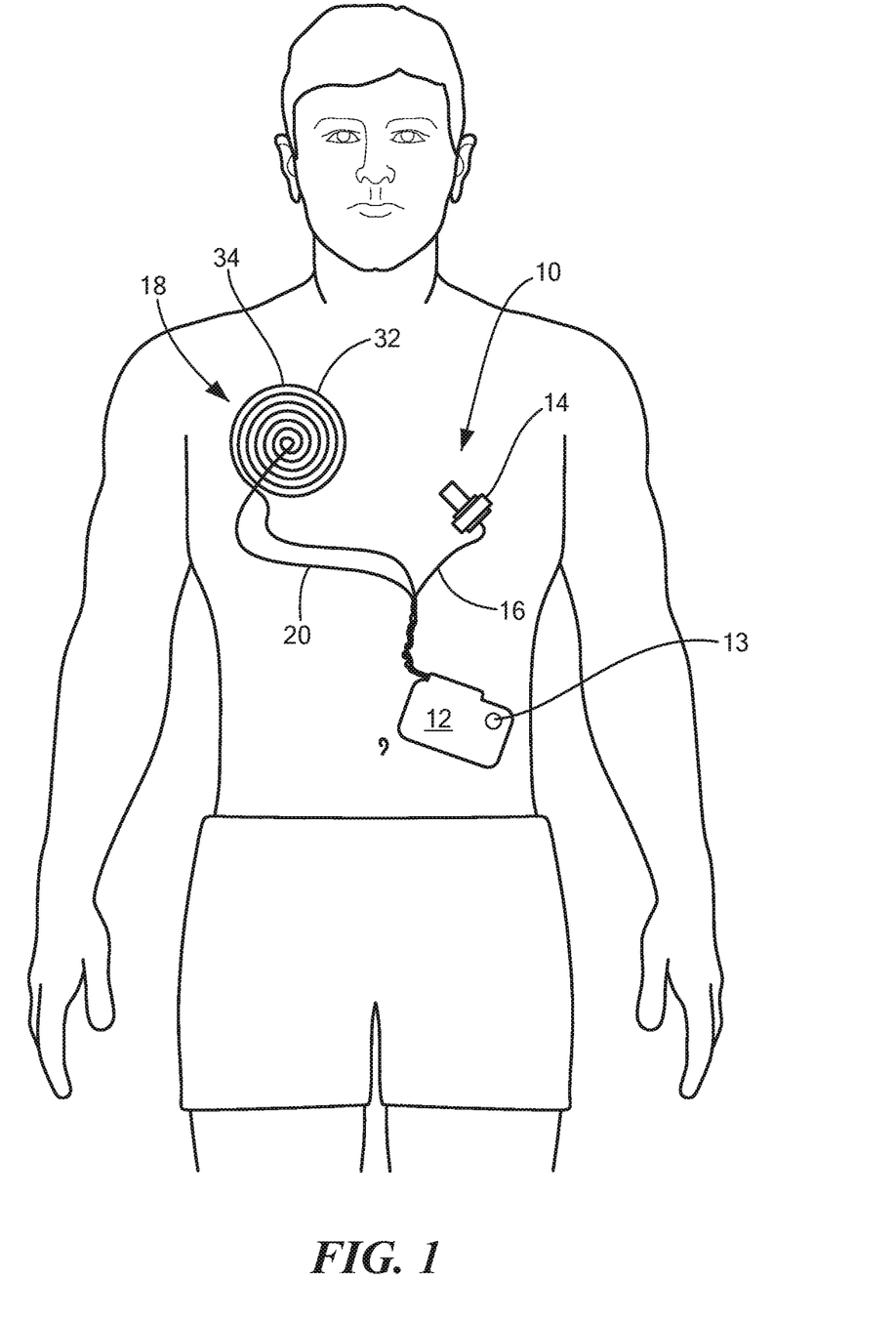
FIG. 1 is a is a front inside of the body view of a patient with a left ventricular assist device, receiving coil, and controller, fully implanted within the patient.
Figure 2:
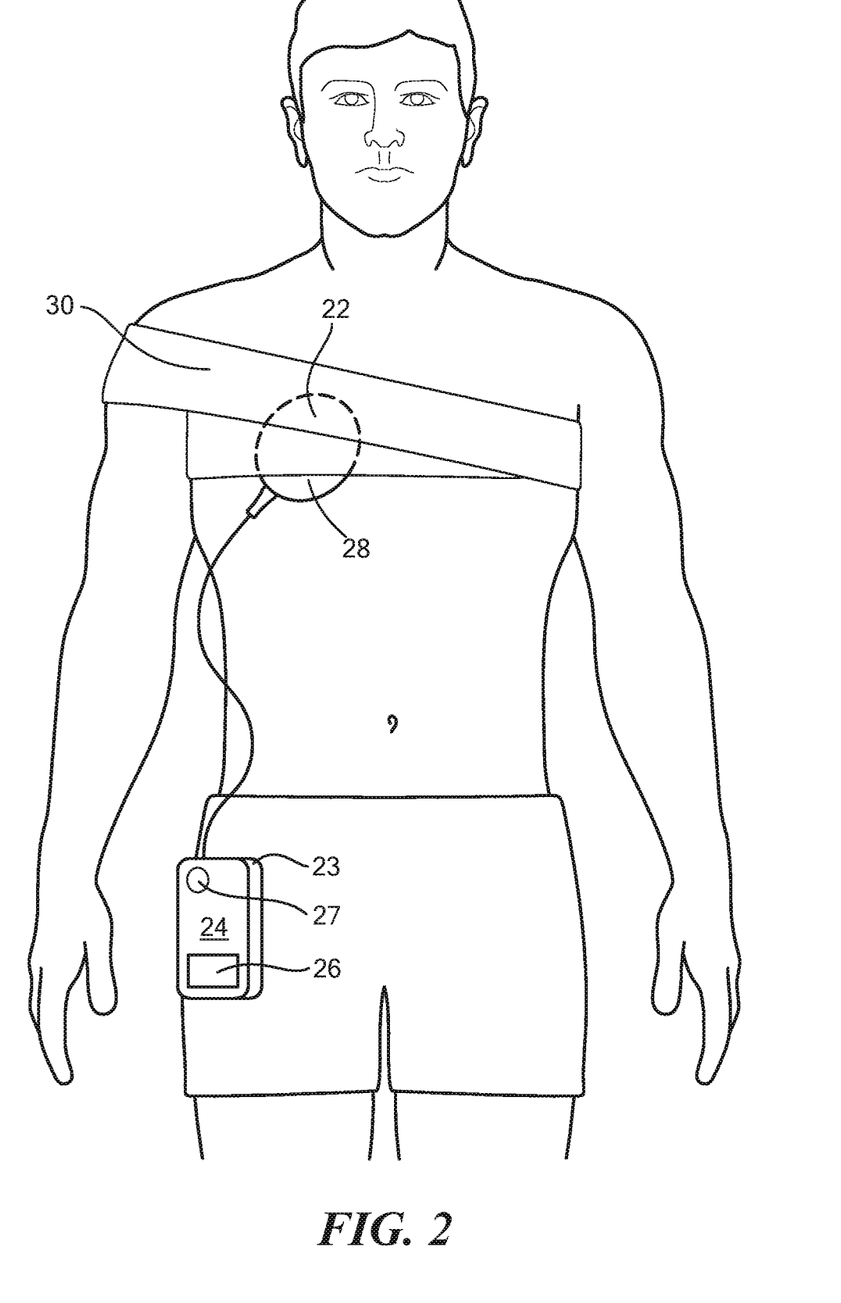
FIG. 2 is a front outside of the body view of the patient shown in FIG. 1 showing a battery and transmission coil coupled to the patient.

Referring now to the drawings in which like reference designators refer to like elements there is shown in FIGS. 1 and 2 an exemplary transcutaneous energy transfer system ("TETS") constructed in accordance with the principles of the present application and designated generally as "10." The TETS 10 may be fully implantable within a patient, whether human or animal, which is to say there are no percutaneous connections between the implanted components of the TETS 10 and the components outside of the body of the patient. In the configuration shown in FIG. 1, the TETS 10 includes an internal controller 12 implanted within the body of the patient. The internal controller 12 may include a power source 13 configured to power the components of the controller and provide power to one or more implantable medical devices, for example, an implantable blood pump such as a ventricular assist device ("VAD") 14 implanted within the left ventricle of the patient's heart. The power source 13 may include a variety of different types of power sources including an implantable battery. VADs 14 may include centrifugal pumps, axial pumps, or other kinds electromagnetic pumps configured to pump blood from the heart to blood vessels to circulate around the body. One such centrifugal pump is the HVAD and is shown and described in U.S. Pat. No. 7,997,854, the entirety of which is incorporated by reference. One such axial pump is the MVAD and is shown and described in U.S. Pat. No. 8,419,609, the entirety of which is incorporated herein by reference. In an exemplary configuration, the VAD 14 is electrically coupled to the internal controller 12 by one or more implanted conductors 16 configured to provide power to the VAD 14, relay one or more measured feedback signals from the VAD 14, and/or provide operating instructions to the VAD 14.

Continuing to refer to FIG. 1, a receiving coil 18 may also be coupled to the internal controller 12 by, for example, one or more implanted conductors 20. In an exemplary configuration, the receiving coil 18 may be implanted subcutaneously proximate the thoracic cavity, although any subcutaneous position may be utilized for implanting the receiving coil 18. The receiving coil 18 is configured to be inductively powered through the patient's skin by a transmission coil 22 (seen in FIG. 2) disposed opposite the receiving coil 18 on the outside/exterior of the patient's body. For example, as shown in FIG. 2, a transmission coil 22 may be coupled to an external controller 23 having a power source 24, for example, a portable battery carried by the patient. In one configuration, the battery is configured to generate a radiofrequency signal for transmission of energy from the transmission coil 22 to the receiving coil 18. The receiving coil 18 may be configured for transcutaneous inductive communication with the transmission coil 22.

The external controller 23 may further include a display 26 configured to provide information to the patient in one or more ways including audibly, visually, and/or tacitly. Additionally, the external controller 23 may further include processing circuitry 27 which can process and transmit information. The processing circuitry 27 may perform various simple and complex operations including, but not limited to, the amplification of signals, computations, and the movement of data from one place to another. The various simple and complex operations that may be performed by the processing circuitry 27 in the external controller 23 is discussed in more detail below with reference to FIG. 4. The processing circuitry 27 may include one or more processors and memory. The external controller 23 may further comprise software, which is stored in, for example, memory at the external controller 23, or stored in external memory (e.g., database, storage array, network storage device, etc.) accessible by the external controller 23. The software may be executable by the processing circuitry 27. The software may include a client application operable to provide a service to a human or non-human user via the external controller 23, with the support of a host computer.

Referring back to FIG. 2, the transmission coil 22 is optionally housed within sealed packaging 28 to protect the transmission coil 22 and is optionally attached to a sling 30 around the patient's torso to maintain the transmission coil 22 in a fixed position for power transmission to the receiving coil 18. Although the sling 30 is shown in FIG. 2, any fixation device may be utilized to either adhere or otherwise affix the transmission coil 22 to the skin of the patient.

Figure 3:
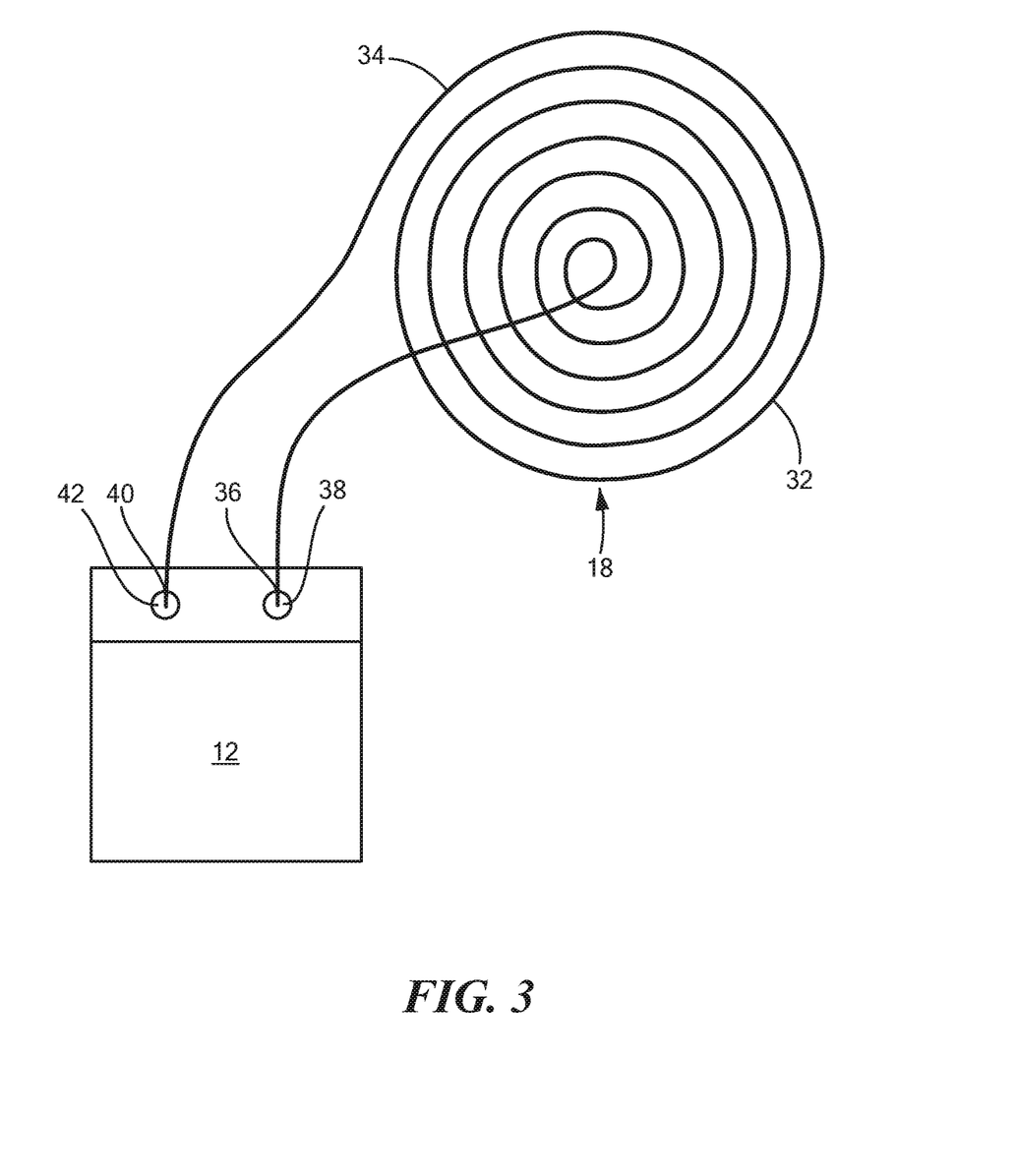
FIG. 3 is a front view of the receiving coil and controller shown in FIG. 1.

Referring now to FIGS. 1 and 3, the receiving coil 18 includes at least one conductor 32 defining a coil 34 and configured to power the VAD 14. The receiving coil 18 may be any shape or size and, for example, in one configuration, the receiving coil 18 may define a substantially planar coil defining a diameter such that is substantially co-planer with an interior surface of the dermis. The receiving coil 18 may be coupled with the internal controller 12 with a first end 36 being electrically coupled to a first coupling 38 of the internal controller 12 and a second end 40 being coupled to a second coupling 42 of the internal controller 12 such that a voltage may be applied to the coil 18. Alternatively, the receiving coil 18 may be coupled with the internal controller 12 using joints or any other configuration. Although not shown, temperature sensors may be found throughout the TETS 10.

Figure 4:
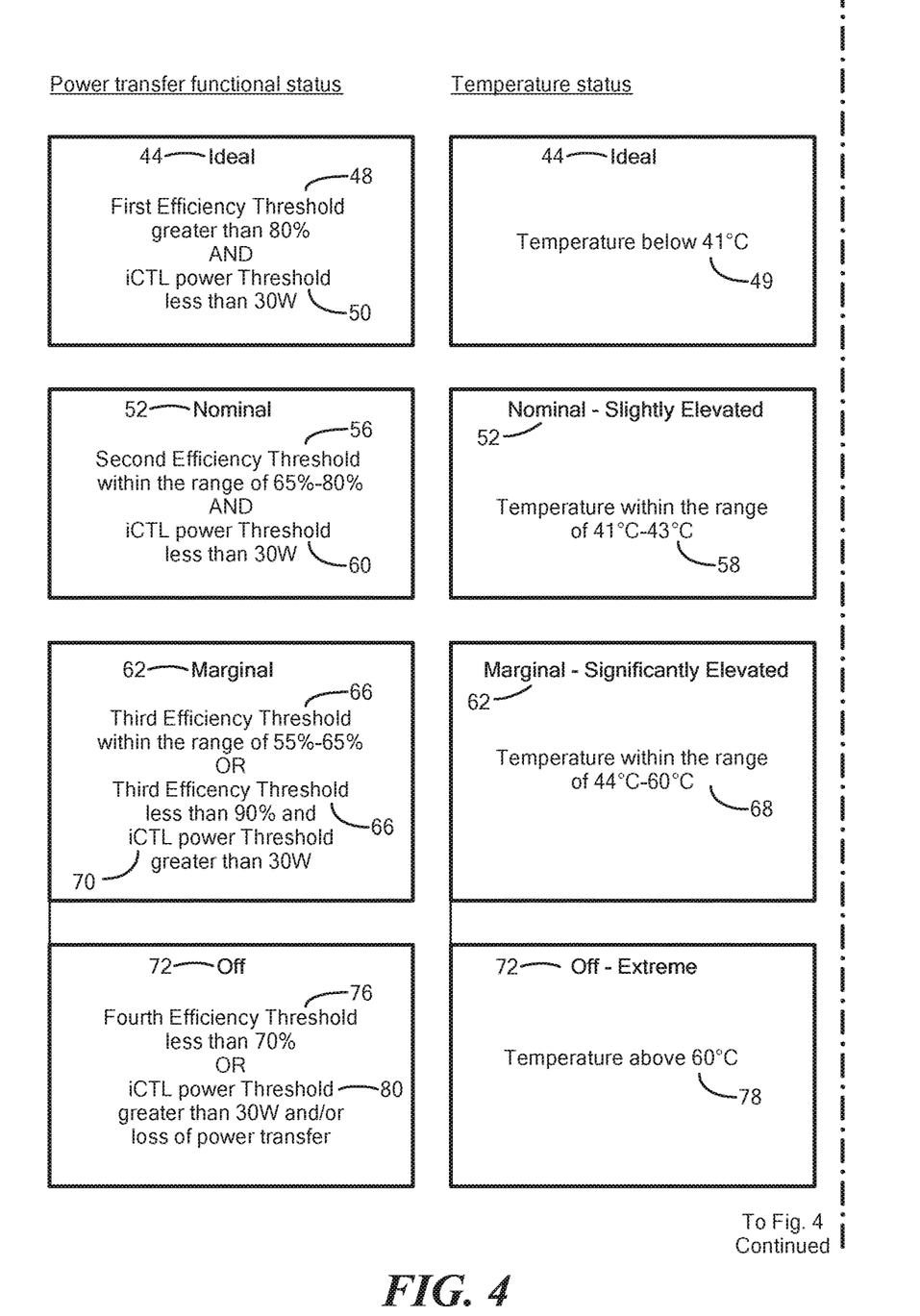
FIG. 4 is a view of exemplary operating conditions associated with the display and corresponding notifications.

Referring now to FIG. 4, the external controller 23 and/or the internal controller 12 may generate a variety of different indicators, including alerts and notifications, which may be shown on the display 26. A particular indicator may be generated by the external controller 23 and/or internal controller 12 and shown on the display 26 as a notification when certain operating conditions/functional status conditions are met. This notification may appear on the display 26 in colors including red, yellow, orange, green, purple, blue, and pink. Alternatively and/or additionally, the visual notification may include a written notification to provide information about the functionality of the TETS 10 as well as to convey information about the urgency of the notification like "immediate attention required." "red alert." "urgent attention required," "too hot," or "not enough energy being transferred to power device." The notifications may also provide information about the functionality of the TETS 10 including, but not limited to the level of the power demand between the transmission coil 22 and the receiving coil 18, the temperature of any portion of the TETS 10 and/or external to the TETS 10 inside the patient's body and/or outside of the patient's body, the implanted battery status as well as other notifications and information. The written indicators may include images designed to draw a person's attention to the display 26 like a large red exclamation point or a red "X." The external controller 23 and/or the internal controller 12 may also have different and additional visual, audile, and/or tactile indicators, notifications, and/or alerts. For example, when a non-critical notification is being provided, a portion of the TETS 10 may vibrate to convey the notification. If there are notifications which are more urgent, there may be audible alerts that increase in loudness to draw the attention of the patient and/or a person near the patient. This information from the indicators may be used to categorize the functional status of the TETS 10 and to translate the functional status into actionable items.

FIG. 4 is an exemplary embodiment with four different operating conditions that may be programmed into the processing circuitry 27 to trigger different notifications which may appear on the display 26 when certain operating conditions are met. As shown in FIG. 4, these operating conditions may include the functional status of the power transfer as well as the temperature status. Some of the operating conditions of the TETS 10 may be programmed not generate the indicator, notification, or alert while other operating conditions may be programmed to generate the indicator, notification, or alert. The determination of which operating conditions may be programmed into the processing circuitry 27 to generate notifications and/or alerts may be based upon the functional/operational requirements of the particular type of TETS 10 being used and may also be based upon how much information is to be provided about the functionality/operation of the TETS 10. Also, the processing circuitry 27 may be programmed so that certain combinations of operating conditions/functional status determinations generate the indicator, alert, or the notification based upon different inputs and criteria.

In this non-limiting example in FIG. 4, the four different operating conditions may include preset parameters relating to, for example: when the power efficiency transfer between the transmission coil 22 and the receiving coil 18 is above a certain level, between certain preset parameters, and/or drops below a certain level; when the temperature of the transmission coil 22 is below a particular temperature, is between a present temperature parameter, or rises above a particular temperature; when the internal controller 12 power demand is below a particular level, between certain preset parameters, or rises above a particular level; and/or when the internal controller 12 power level falls to a specified level. Any individual parameter and/or set of parameters may be used to trigger certain operating conditions in the processing circuitry 27. The determination of which operating conditions to use and the parameters defining each of the operating conditions may be based upon what type of medical device the TETS 10 is being used to power as well as the requirements of the particular patient.

While a patient is wearing the TETS 10, constant monitoring may be occurring to determine how the TETS 10 is functioning/operating. The external controller 23 and/or the internal controller 12 may continually monitor how efficiently energy is being exchanged, the transmission coil 22 temperature, the power demand of the internal controller 12, and/or the internal controller 12 power level. This information may be stored and may later be accessed so that, for example, a medical provider may see how the TETS 10 is functioning/operating over a period of time.

When a patient has the TETS 10, the patient may move and reposition when asleep or awake and this movement may impact the functional status of the TETS 10 including the power efficiency transfer between the transmission coil 22 and the receiving coil 18, the temperature of the transmission coil 22, the internal controller 12 power demand, and/or the internal controller 12 power level based upon the physical positioning of the patient. Accordingly, a delay may be programmed into the external controller 23 and/or the internal controller 12 such that when any of the parameters in a particular operating condition is/are met, there is a delay before any notification is triggered as, for example, another movement may "correct" the particular functionality and/or operating condition that was initially triggering an alert and/or notification. This delay may help avoid unnecessary notifications when there is transient movement of the transmission coil 22 and the receiving coil 18 away from their intended positions but return without patient intervention. This movements may, for example, be a reaching motion by the individual with the TETS 10. If the first operating condition 44 is triggered during this reaching movement, there may be a couple second delay before any alarms, notifications, or indicators are activated by the external controller 23 and/or the internal controller 12.

As shown in FIG. 4, different operating conditions/functional status conditions may be programmed into the external controller 23 and/or the internal controller 12 which include certain preset parameters. As a non-limiting example, the operating conditions, which may include the functional status of the power transfer as well as the temperature status, may have preset parameters which are to designate when the operation of the TETS 10 is "Ideal," "Nominal", "Marginal", and "Off." For example, a first operating condition 44 may be when the operation off the TETS 10 is "ideal" which means that system is working properly and does not require the attention of the user. The first operating condition 44 may trigger a first notification 46 in the external controller 23 and/or the internal controller 12 if any one or more than one of the preset parameters of the first operating condition 44 are met. One of the preset parameters may be when the energy transfer between the receiving coil 18 and the transmission coil 22 is within a particular range, rises above, or fall below a particular level, which may be designated as a first predetermined threshold 48. Another preset parameter may be when the temperature of the transmission coil 22 is within a particular range, rises above, or falls below a particular temperature, which may be designed as a first predetermined transmission coil temperature 49. Temperature may be considered as separate functional status/operating condition that may a preset parameter or temperature may be considered in combination with any of the preset parameters. The TETS 10 may have a variety of different temperature sensors in different locations including inside the patient's body as well as on the exterior of the body. Accordingly, internal and external temperatures may independently be set to trigger a notification in the external controller 23 and/or the internal controller 12. A third preset parameter may be when the power demand of the internal controller 12 is within a particular range, rises above, or falls below a particular level, which may be designed as a first predetermined internal controller power demand 50. When any one and/or any combination of these preset parameters of the first operating condition 44 are met, the external controller 23 and/or the internal controller 12 may generate the first notification 46 which is shown on the display 26. Alternatively, a combination of these preset parameters may generate the first notification 46 on the display 26.

Continuing to refer to FIG. 4, the first operating condition 44 may be triggered when the power efficiency transfer between the transmission coil 22 and the receiving coil 18 is at a first predetermined threshold 48 and/or when a first predetermined internal controller power demand 50 is met. When the transmission coil 22 and the receiving coil 18 are misaligned, the power efficiency transfer between the transmission coil 22 and the receiving coil 18 may drop. As the receiving coil 18 and the transmission coil 22 become farther misaligned, the efficiency of the power transfer between the receiving coil 18 and the transmission coil 22 decreases by a percentage from 100%. As a non-limiting example, the first predetermined threshold 48 may be met when the efficiency of the power transfer between the receiving coil 18 and the transmission coil 22 is greater than 80%. This may generally indicate that the power transfer between the transmission coil 22 and the receiving coil 18 is occurring "ideally." It will be noted that any preset parameter may be used for any of the thresholds.

The first operating condition 44 may also be triggered when the first predetermined transmission coil temperature 49 is met. For example, when the temperature of the transmission coil 22 is below 41 degrees centigrade (° C.), the first operating condition 44 may be triggered to indicate that the temperature is "ideal". The first operating condition 44 may also be triggered when the first predetermined internal controller power demand 50 is met. As shown as a non-limiting example in FIG. 4, the first predetermined internal controller power demand 50 may be when the internal controller 12 power demand (also "iCTL power") is less than 30 Watts ("W").

Additionally, the first operating condition 44 may be met when certain combinations of preset parameters are met. As shown in FIG. 4, the first operating condition 44 may be met when both the first predetermined threshold 48 and the first predetermined internal controller power demand 50 are met. Furthermore, if the first predetermined threshold 48, the first predetermined internal controller power demand 50, and temperatures within the first predetermined transmission coil temperature 49 are all met, the first operating condition 44 may also be met.

Continuing to refer to FIG. 4, when the first operating condition 44 is triggered by any of the specified preset parameters or any combination of these preset parameters, the external controller 23 and/or the internal controller 12 may have certain words or images on the display 26 and/or may include audile and/or a tactile indicators as part of the first notification 46. The first notification 46 may include words on the display 26, for example, like "alignment is good enough-Ideal," "functionality is ideal," "Power transfer status is ideal or nominal and temperatures are nominal," "ideal", "perfect." "good," or another suitable textual description to provide information to an individual reading the display 26 to indicate that the functionality of the TETS 10 is generally working well. Additional information about the functionality/status of the TETS 10 may also be on the display 26 including specific information about the power efficiency transfer between the transmission coil 22 and the receiving coil 18, the temperature of the transmission coil 22, the power demand of the internal controller 12, and/or the internal controller power level. The first notification 46 on the display 26 may also appear in a color such as green and may also be accompanied by a chiming or other noise that is designated to indicate that the functionality of the TETS 10 is working well. A user may select the designated noise that s/he will hear when the first operating condition 44 is met, or this may be preset into the system.

The algorithm that determines what notifications to provide to the user relative to the power transfer between the transmission coil 22 and the receiving coil 18 may not be based solely on efficiency or coupling. For example, the quality of the coil alignment may need to be better under some specific power demand conditions. For example, in the case of a thrombus event in the patient using the TETS 10, the pump, such as the VAD 14, may require a significant amount of power to maintain operations. Any notification provided may indicate, for example, that the transmission coil 22 and the receiving coil 18 need to be better aligned to meet the power demand requirements of the pump (the VAD 14) during the thrombus event. This type of notification may occur to ensure that the necessary power levels to the TETS 10 are met so that the pump (the VAD 14) may continue operating during an event that may require a significant amount of power. Additional information may be provided in the notification to indicate how the TETS 10 is operating, if anything may need attention, and/or about the event that the patient is currently experiencing.

Continuing to refer to FIG. 4, as another non-limiting example, a second operating condition 52 may be triggered by the external controller 23 and/or the internal controller 12 and a second notification 54 may be generated based upon certain preset parameters or a combination of preset parameters which are programmed into the external controller 23 and/or the internal controller 12. One of the preset parameters that may be associated with the second operating condition 52 may be when the energy transfer between the receiving coil 18 and the transmission coil 22 falls below a specified level, which may be lower than and/or the same as the level associated with the first predetermined threshold 48, and which may be designated as a second predetermined threshold 56. Another preset parameter may be when the temperature of the transmission coil 22 rises above the temperature identified in the first predetermined transmission coil temperature 49, and which may be designed as a second predetermined transmission coil temperature 58. Another preset parameter may be when the power demand of the internal controller 12 rises above the level of the first predetermined internal controller power demand 50 and/or may be the same as the first predetermined internal controller power demand 50, which may be designated as a second predetermined internal controller power demand 60. When any of these preset parameters and/or a combination of these preset parameters in the second operating condition 52 are met, the external controller 23 and/or the internal controller 12 may generate the second notification 54 which may be shown on the display 26.

Continuing to refer to FIG. 4 when the functionality of the TETS 10 meets any one and/or a combination of the parameters set in the second operating condition 52, a notification may appear that indicates that the TETS is functioning/performing "nominally" and does not require immediate the attention of the user. For example, the second operating condition 52 may be triggered when there is a misalignment between the transmission coil 22 and the receiving coil 18 which causes the power efficiency transfer between the transmission coil 22 and the receiving coil 18 to be at the second predetermined threshold 56 and/or below the first predetermined threshold 48. As a non-limiting example and as shown in FIG. 4, the second predetermined threshold 56 may be when the efficiency of the power transfer between the receiving coil 18 and the transmission coil 22 is between 65-80%. The second operating condition 52 may also be triggered when the second predetermined transmission coil temperature 58 is met, for example, when the temperature of the transmission coil 22 is within the range of 41° C. and 43° C. and this temperature range may be considered slightly elevated.

Furthermore, the second operating condition 52 may also be triggered when the second predetermined internal controller power demand 60 is met which, in FIG. 4, is shown as when the internal controller 12 power demand is less than 30 W. Additionally, the second operating condition 52 may be met when certain combinations of preset parameters are met. As shown in FIG. 4, the second operating condition 52 may be met when the second predetermined threshold 56 is met and when the second predetermined internal controller power demand 60 is met. Furthermore, the second operating condition 52 may be met when the second predetermined threshold 56 and the second predetermined internal controller power demand 60 are met along with temperatures which are at or below the second predetermined transmission coil temperature 58.

Continuing to refer to FIG. 4 when the functional operation is in the second operating condition 52, when any of the preset parameters defining the second operating condition 52 are met, the external controller 23 and/or the internal controller 12 may show particular words or images on the display 26 and/or may include audile and/or a tactile indicators and may appear as the second notification 54. As shown in FIG. 4, the second notification 54 on the display 26 may include words like, for example, "alignment is Ok,"

"that the functionality is Nominal," "Power transfer status is Nominal," "Nominal," "acceptable." "ok." "temperature is ideal," or another suitable textual description to provide information to an individual reading the display 26. Additional information about the functionality of the TETS 10 may also be shown on the display 26. Furthermore, the second notification 54 on the display 26 may appear in green or yellow and/or include a beeping or other noise designed to indicate that the functionality is working acceptably/nominally at this time. A user may select the designated noise, or this may be preset.

Continuing to refer to FIG. 4, a third operating condition 62 may be triggered by the external controller 23 and/or the internal controller 12 and a third notification 64 may be generated based upon certain preset parameters which are programmed into the external controller 23 and/or the internal controller 12. One of the preset parameters associated with the third operating condition 62 may be when the energy transfer between the receiving coil 18 and the transmission coil 22 fall below a level and/or is the same or similar as the level associated with the first predetermined threshold 48 and which may also be designated as the third predetermined threshold 66. Another preset parameter may be when the temperature of the transmission coil rises above the temperature identified in the second predetermined transmission coil temperature 58, and which may be designed as a third predetermined transmission coil temperature 68. Another third preset parameter may be when the power demand of the internal controller rises above the level of the second predetermined internal controller power demand 60, which may be designated as a third predetermined internal controller power demand 70. When any of these preset parameters and/or combination of the preset parameters of the third operating condition 62 are met, the external controller 23 and/or the internal controller 12 may generate the third notification 64 which is shown on the display 26.

Continuing to refer to FIG. 4 when the functional operation is in the third operating condition 62, there may be preset parameters which define when the TETS 10 is operating "poorly" and may require attention of the user so that the TETS 10 may continue to operate. For example, the third operating condition 62 may be triggered when there is a misalignment of the transmission coil 22 and the receiving coil 18 which causes a power efficiency transfer between the transmission coil 22 and the receiving coil 18 to drop to a preset range. As a non-limiting example and as shown in FIG. 4, the third predetermined threshold 66 may be met when the efficiency of the power transfer between the receiving coil 18 and the transmission coil 22 is within the range of 55-65% The third operating condition 62 may also be triggered when the third predetermined transmission coil temperature 68 is met, for example, when the temperature of the transmission coil 22 is within the range of 44° C. and 60° C. as shown in FIG. 4 which may also be considered as a significantly elevated temperature. Furthermore, the third operating condition 62 may also be triggered when the third predetermined internal controller power demand 70 is met which, in FIG. 4, is when the internal controller 12 power demand is greater than 30 W. Additionally, the third operating condition 62 may be met when certain combinations of preset parameters are met. As shown in FIG. 4, the third operating condition 62 may be met when the third predetermined threshold 66 is when the power efficiency transfer between the transmission coil 22 and the receiving coil 18 is less than 80% and the third predetermined internal controller power demand 70 is when the internal controller 12 power demand is greater than 30 W. Additionally, the third operating condition 62 may be met when the power efficiency transfer between the transmission coil 22 and the receiving coil 18 is within the range of 55-65%. Different transmission coil 22 temperatures may also indicate which functional status is triggered as well.

Continuing to refer to FIG. 4, when the functional operation of the external controller 23 and/or the internal controller 2 is operating in the third operating condition 62, when any of the preset parameters defining the third operating condition 62 are met, the external controller 23 and/or the internal controller 12 may show particular words or images on the display 26 and/or may include audile and/or a tactile indicators and may appear as the third notification 64. As shown in FIG. 4, the third notification 64 on the display 26 may include words like, for example, "Alignment is Marginal and Should be Improved." "Functionality is Marginal and Needs Improvement," "power transfer status is marginal," "temperatures are elevated," "Marginal," "Needs Improvement," or another suitable textual description to provide information to an individual reading the display 26 to indicate that the TETS 10 may require attention immediately. Additional information about the functionality of the TETS 10 may also be on the display 26. Furthermore, the third notification 64 on the display 26 may appear in orange and/or yellow and/or include a beeping or other audible sound designed to indicate that the immediate attention is required. A user may select the designated sound, or this may be preset. The TETS 10 may also vibrate when any or all of the preset parameters defining the third operating condition 62 are met. Generally, the third operating condition 62 is associated with a poor efficiency, but an energy transfer a certain power threshold will still be occurring. If the TETS 10 is operating near the limits of heating and/or SAR, the internal controller 12 power source 13 charging may be suspended and/or reduced to prevent injury to the patient. In this type of situation, the user may be prompted to improve alignment or take another corrective action to keep the device functioning.

Continuing to refer to FIG. 4, a fourth operating condition 72 may be triggered by the external controller 23 and/or the internal controller 12 and a fourth notification 74 may be generated based upon certain preset parameters and/or a combination of preset parameters which are programmed into the external controller 23 and/or the internal controller 12. One of the preset parameters associated with the fourth operating condition 72 may be when the energy transfer between the receiving coil 18 and the transmission coil 22 fall below a level, which may be lower than the level associated with the third predetermined threshold 66, and which may be designated as a fourth predetermined threshold 76. Another preset parameter may be when the temperature of the transmission coil 22 rises above the temperature identified in the third predetermined transmission coil temperature 68, and which may be designed as a fourth predetermined transmission coil temperature 78. A third preset parameter may be when the power demand of the internal controller rises above the level of the third predetermined internal controller power demand 70, which may be designated as a fourth predetermined internal controller power demand 80 and/or when there is a loss of power transfer. The fourth operating condition 72 may have preset parameters which define when TETS 10 is "off" and requires the immediate attention of the user.

Continuing to refer to FIG. 4, when the functional operation of the external controller 23 and/or the internal controller 12 is in the fourth operating condition 72, there may be preset parameters which define when TETS 10 should be turned "off" and/or may require the immediate or urgent attention of the user so that TETS 10 can continue to operate. The TETS 10 may be turned off and/or an urgent notification may be generated when either one and/or a combination of the preset parameters that define the fourth operating condition 72 are met given potential safety and functional/operational issues with the TETS 10. For example, the fourth operating condition 72 may be triggered when there is a misalignment of the transmission coil 22 and the receiving coil 18 which causes a power efficiency transfer between the transmission coil 22 and the receiving coil 18 to drop below the fourth predetermined threshold 76. As a non-limiting example, and as shown in FIG. 4, the fourth predetermined threshold 76 may be met when the efficiency of the power transfer between the receiving coil 18 and the transmission coil 22 is less than 70%. This may indicate that the power transfer is very poor. The fourth operating condition 72 may also be triggered when the fourth predetermined transmission coil temperature 78 is met, for example, when the temperature of the transmission coil 22 rises above 60° C., which may also be considered an extreme temperature. Furthermore, the fourth operating condition 72 may also be triggered when the fourth predetermined internal controller power demand 80 is met which, in FIG. 4, is when the internal controller 12 power demand is greater than 30 W and/or when there is a loss of power transfer. Additionally, the fourth operating condition 72 may be triggered when the third predetermined threshold 76 is met and/or the third predetermined internal controller power demand 70 is met and the temperature of the transmission coil 22 is 43° C. or greater.

Continuing to refer to FIG. 4, when the functional operation of the external controller 23 and/or the internal controller 12 is in the fourth operating condition 72, when one and/or any combination of the preset parameters defining the fourth operating condition 72 are met, the external controller 23 may turn off the TETS 10 and/or generate a notification. The external controller 23 and/or the internal controller 12 may show particular words or images on the display 26 and/or may include audile and/or a tactile indicator and may appear as the fourth notification 74. As shown in FIG. 4, the fourth notification 74 on the display 26 may include words like, for example, "Loss of External Power," "Alignment is Bad and Needs To Be Improved." "Functionality is Bad and needs improvement," "no power transfer," "Bad," "Off," "Immediate Attention Required." "Alignment is marginal and temperature is significantly elevated," or another suitable textual description to provide information to an individual reading the display 26 to indicate that the TETS 10 requires attention immediately and that the TETS 10 has been turned off. Additional information about the functionality of the TETS 10 may also be on the display 26. Furthermore, the fourth notification 74 on the display 26 may appear in red or orange and/or include a beeping or other noise designed to indicate that the functionality of TETS 10 has been turned off or suspended. A user may select the designated noise, or this may be preset. Generally, the fourth operating condition 72 is associated with an efficiency that is poor and therefore it is no longer feasible to maintain the energy transfer within the heating/SAR limits. The transmission of power may stop attempting to transfer energy until alignment between the receiving coil 18 and the transmission coil 22 is improved. Periodic short duration energy pulses may be applied to TETS 10 to determine if it's appropriate to reinitiate full energy transfer.

During operation of the TETS 10, a combination of the operating conditions may be met at the same time. For example, the first operating condition 44, the second operating condition 52, the third operating condition 62, and/or the fourth operating condition 72 may be triggered simultaneously. If two different operating conditions are met at the same time, the notification may default to the higher priority condition that may require a more urgent response. In an exemplary embodiment, if any of the preset parameters in the second operating condition 52 are met at the same time as any of the preset parameters in the third operating condition 62, the third operating condition 62 may be triggered by the external controller 23 and/or the internal controller 12 and the third notification 64 may be generated based upon certain preset parameters which are programmed into the external controller 23 and/or the internal controller 12.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A transcutaneous energy transfer system, comprising:
an external controller having a power source and a processing circuitry;
a transmission coil in communication with the external controller;
a receiving coil configured for transcutaneous inductive communication with the transmission coil; and
an implantable controller in communication with the receiving coil and an implantable blood pump, the implantable controller having a battery configured to receive power from the receiving coil,
the processing circuitry being configured to:
determine, based on a temperature of the transmission coil and a power transfer efficiency between the transmission coil and the receiving coil, an operating condition of the processing circuitry from a plurality of operating conditions, wherein each operating condition of the plurality of operating conditions is associated with a corresponding urgency of user intervention, and wherein the plurality of operating conditions comprises:
a first operating condition associated with no urgency of user intervention, wherein the first operating condition occurs when the temperature of the transmission coil is below a first predetermined transmission coil temperature and when the power transfer efficiency between the transmission coil and the receiving coil is above a first predetermined threshold of at least 80%;
a second operating condition associated with a mild urgency of user intervention, wherein the second operating condition occurs when either the power transfer efficiency between the transmission coil and the receiving coil drops below a second predetermined threshold between 65% and 80% or the temperature of the transmission coil rises above a second predetermined transmission coil temperature; and
generate a notification associated with the operating condition of the processing circuitry.

2. The system of claim 1, wherein the plurality of operating conditions further comprises:

a third operating condition associated with a moderate urgency of user intervention, wherein the third operating condition occurs when either the power transfer efficiency between the transmission coil and the receiving coil drops below a third predetermined threshold or the temperature of the transmission coil rises above a third predetermined transmission coil temperature; and a fourth operating condition associated with a high urgency of user intervention, wherein the fourth operating condition occurs when either the power transfer efficiency between the transmission coil and the receiving coil is below a fourth predetermined threshold or there is a loss of power transfer between the transmission coil and the receiving coil.

3. The system of claim 1, wherein the external controller further includes a display.

4. The system of claim 2, wherein the third predetermined threshold is within the range of 55% to 65%.

5. The system of claim 2, wherein the second predetermined transmission coil temperature is within the range of 41° C. to 43° C.

6. The system of claim 2, wherein the third predetermined transmission coil temperature is within the range of 44° C. to 60° C.

7. The system of claim 2, wherein the first predetermined transmission coil temperature is below 41° C.

8. The system of claim 2, wherein the first operating condition occurs when an internal controller power demand is less than a predetermined power demand threshold, wherein the second operating condition occurs when the internal controller power demand is less than the predetermined power demand threshold, wherein the third operating condition occurs when the internal controller power demand is greater than the predetermined power demand threshold, and wherein the fourth operating condition occurs when the internal controller power demand is greater than the predetermined power demand threshold.

9. The system of claim 8, wherein the predetermined power demand threshold is 30 Watts.

10. A method comprising:
obtaining, by processing circuitry, a temperature of a transmission coil of a transcutaneous energy transfer system and a power transfer efficiency between the transmission coil and a receiving coil of the transcutaneous energy transfer system, wherein the transcutaneous energy transfer system comprises:
an external controller having the processing circuitry;
the transmission coil;
the receiving coil; and
an implantable controller in communication with the receiving coil and an implantable blood pump;
determining, based on the temperature of the transmission coil and the power transfer efficiency between the transmission coil and the receiving coil, an operating condition of the processing circuitry from a plurality of operating conditions, wherein each operating condition of the plurality of operating conditions is associated with a corresponding urgency of user intervention, and wherein the plurality of operating conditions comprises:
a first operating condition associated with no urgency of user intervention, wherein the first operating condition occurs when the temperature of the transmission coil is below a first predetermined transmission coil temperature and when the power transfer efficiency between the transmission coil and the receiving coil is above a first predetermined threshold of at least 80%;
a second operating condition associated with a mild urgency of user intervention, wherein the second operating condition occurs when either the power transfer efficiency between the transmission coil and the receiving coil drops below a second predetermined threshold between 65% and 80% or the temperature of the transmission coil rises above a second predetermined transmission coil temperature; and
generating a notification associated with the operating condition of the processing circuitry.

11. The method of claim 10, wherein the plurality of operating conditions further comprises:
a third operating condition associated with a moderate urgency of user intervention, wherein the third operating condition occurs when either the power transfer efficiency between the transmission coil and the receiving coil drops below a third predetermined threshold or the temperature of the transmission coil rises above a third predetermined transmission coil temperature; and
a fourth operating condition associated with a high urgency of user intervention, wherein the fourth operating condition occurs when either the power transfer efficiency between the transmission coil and the receiving coil is below a fourth predetermined threshold or there is a loss of power transfer between the transmission coil and the receiving coil.

12. The method of claim 11, wherein the third predetermined threshold is within the range of 55% to 65%.

13. The method of claim 11, wherein the second predetermined transmission coil temperature is within the range of 41° C. to 43° C.

14. The method of claim 11, wherein the third predetermined transmission coil temperature is within the range of 44° C. to 60° C.

15. The method of claim 11, wherein the first predetermined transmission coil temperature is below 41° C.

16. The method of claim 11, wherein the first operating condition occurs when an internal controller power demand is less than a predetermined power demand threshold, wherein the second operating condition occurs when the internal controller power demand is less than the predetermined power demand threshold, wherein the third operating condition occurs when the internal controller power demand is greater than the predetermined power demand threshold, and wherein the second operating condition occurs when the internal controller power demand is greater than the predetermined power demand threshold.

* * * * *